(12) United States Patent
Smith et al.

(10) Patent No.: US 9,456,733 B2
(45) Date of Patent: Oct. 4, 2016

(54) ENDOSCOPIC INSTRUMENT HAVING A DEFLECTABLE DISTAL TOOL

(71) Applicant: Boston Scientific Scimed, Inc., Maple Grove, MN (US)

(72) Inventors: Paul Smith, Smithfield, RI (US); Naroun Suon, Lawrence, MA (US); Samuel Raybin, Marlborough, MA (US); John B. Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/959,058

(22) Filed: Dec. 4, 2015

(65) Prior Publication Data

US 2016/0081532 A1   Mar. 24, 2016

Related U.S. Application Data

(63) Continuation of application No. 13/665,161, filed on Oct. 31, 2012, now Pat. No. 9,226,649.

(60) Provisional application No. 61/553,301, filed on Oct. 31, 2011.

(51) Int. Cl.
| | | |
|---|---|---|
| *A61B 1/00* | (2006.01) | |
| *A61B 1/005* | (2006.01) | |
| *A61B 1/015* | (2006.01) | |
| *A61B 18/14* | (2006.01) | |
| *A61B 18/00* | (2006.01) | |

(52) U.S. Cl.
CPC ......... *A61B 1/00098* (2013.01); *A61B 1/0051* (2013.01); *A61B 1/015* (2013.01); *A61B 18/1442* (2013.01); *A61B 18/1477* (2013.01); *A61B 18/1492* (2013.01); *A61B 2018/00595* (2013.01); *A61B 2218/002* (2013.01)

(58) Field of Classification Search
None
See application file for complete search history.

(56) References Cited

U.S. PATENT DOCUMENTS

| | | |
|---|---|---|
| 4,187,849 A | 2/1980 | Stim |
| 4,452,236 A | 6/1984 | Utsugi |
| 5,704,899 A | 1/1998 | Milo |
| 6,238,336 B1 | 5/2001 | Ouchi |
| 6,824,509 B2 | 11/2004 | Yamaya et al. |
| 2003/0040657 A1 | 2/2003 | Yamaya et al. |
| 2003/0073902 A1 | 4/2003 | Hauschild et al. |

(Continued)

FOREIGN PATENT DOCUMENTS

| | | |
|---|---|---|
| EP | 1 426 005 A1 | 6/2004 |
| EP | 1 849 416 A2 | 10/2007 |

(Continued)

OTHER PUBLICATIONS

International Search Report of PCT/US2012/062745 dated Feb. 6, 2013 (3 pages).

*Primary Examiner* — Brian T Gedeon
*Assistant Examiner* — Ankit D Tejani
(74) *Attorney, Agent, or Firm* — Bookoff McAndrews, PLLC

(57) ABSTRACT

Embodiments of the disclosure may include a medical device comprising a flexible elongate member including a longitudinal axis and a tool connected to the elongate member at a pivot axis, wherein the tool may be configured to conduct electricity and deliver a fluid, and wherein the tool may be configured to pivot towards either side of the longitudinal axis relative to the elongate member at the pivot axis.

20 Claims, 4 Drawing Sheets

(56) References Cited

U.S. PATENT DOCUMENTS

| | | |
|---|---|---|
| 2004/0186368 A1 | 9/2004 | Ramzipoor et al. |
| 2006/0289602 A1 | 12/2006 | Wales et al. |
| 2007/0270895 A1 | 11/2007 | Nobis et al. |
| 2007/0282353 A1 | 12/2007 | Surti |
| 2008/0167665 A1* | 7/2008 | Arp ............... A61B 17/1285 606/142 |
| 2009/0012517 A1 | 1/2009 | de la Rama et al. |
| 2009/0171349 A1 | 7/2009 | Byrd et al. |
| 2010/0076266 A1 | 3/2010 | Baulais et al. |
| 2010/0168718 A1* | 7/2010 | Bellisario ............ A61M 39/10 604/533 |
| 2010/0222677 A1 | 9/2010 | Placek et al. |
| 2010/0280316 A1 | 11/2010 | Dietz et al. |
| 2011/0224647 A1 | 9/2011 | Lazarus |

FOREIGN PATENT DOCUMENTS

| | | |
|---|---|---|
| EP | 1 857 061 A1 | 11/2007 |
| WO | WO 99/05975 A1 | 2/1999 |
| WO | WO 02/094353 A2 | 11/2002 |

\* cited by examiner

ENDOSCOPIC INSTRUMENT HAVING A DEFLECTABLE DISTAL TOOL

CROSS-REFERENCE TO RELATED APPLICATION

This application is a continuation of U.S. application Ser. No. 13/665,161, filed Oct. 31, 2012, now U.S. Pat. No. 9,226,649, which claims the benefit of priority under 35 U.S.C. §119 to U.S. Provisional Patent Application No. 61/553,301, filed on Oct. 31, 2011, all of which are incorporated herein by reference in their entireties.

FIELD OF THE DISCLOSURE

Embodiments of the present disclosure include medical devices, and more particularly, endoscopic instruments having a deflectable distal tool, for example, a deflectable injection needle, and related methods of using such medical devices.

BACKGROUND OF THE DISCLOSURE

Generally speaking, endoscopes may be used for various diagnostic and medical procedures. Endoscopes may be used for the diagnosis and treatment of a wide range of diseases and disorders that typically require a physician to access and navigate internal anatomical lumens within a patient's body. Once the endoscope is positioned in a desired body portion, a treatment instrument may be advanced through a working channel of the endoscope to the desired body portion.

For example, in certain tissue dissection procedures, an electrocautery needle may be directed through the working channel of the endoscope, and the endoscope may be maneuvered to a desired tissue location. The needle may be configured to cauterize certain target tissue, such as, for example, adenomas (i.e., tumors attached to a bodily surface). Once the needle reaches the desired portion of tissue, an electrical current may run through the needle, and the needle may then resect and/or cauterize the target tissue.

A conventional electrocautery needle may be positioned relative to the target tissue by movement of the endoscope. In other words, the endoscope is articulated, steered, shifted, pulled, and/or pushed by the physician to place the needle at or near the target tissue. A second operator, such as another physician or a physician's assistant, may then control the operation of the needle once positioned at or near the target tissue.

Adjusting the position of the electrocautery needle by moving the endoscope may be time consuming, cumbersome, and not accurate. Accordingly, a need exists to simplify the manner and improve the accuracy in which the position of an electrocautery needle is adjusted. The injection needle and related methods of the present disclosure are directed to improvements in the existing technology.

SUMMARY OF THE DISCLOSURE

In accordance with an embodiment, a medical device may include a flexible elongate member including a longitudinal axis and a tool connected to the elongate member at a pivot axis, wherein the tool may be configured to conduct electricity and deliver a fluid, and wherein the tool may be configured to pivot towards either side of the longitudinal axis relative to the elongate member at the pivot axis.

Various embodiments of the disclosure may include one or more of the following aspects: a positioning mechanism, wherein actuation of the positioning mechanism may cause the tool to pivot; the positioning system may include a clevis, a pivoting member held by the clevis and rotatable relative to the clevis, and at least one control member connected to the pivoting member, wherein the tool may be operably coupled to the pivoting member; the tool may be deflected in a first direction when the at least one control member is distally advanced, and the tool may be deflected in a second direction opposite the first direction when the at least one control member is proximally retracted; the at least one control member may include a first control member and a second control member, wherein the tool may be deflected in a first direction when the first control member is distally advanced, and the tool may be deflected in a second direction opposite the first direction when the second control member is distally advanced; a flexible delivery fluidly coupled to the tool, wherein the delivery tube may be configured to deliver fluid to the tool; the delivery tube may provide an electrical pathway to the tool; the delivery tube may include a flexible distal portion formed of an inner coil covered by an outer polymeric sheath; and the at least one control member may be only one control member, and the tool may be a hollow tube with a distal opening.

In accordance with another embodiment, a medical device may include a flexible elongate member including a longitudinal axis, a tool configured to conduct electricity and deliver a fluid, and a pivoting member. The pivoting member may couple the tool to the elongate member, wherein the tool may be configured to pivot towards either side of the longitudinal axis relative to the elongate member by actuation of the pivoting member, wherein the pivoting member may include a lumen extending to the tool.

Various embodiments of the disclosure may include one or more of the following aspects: a flexible delivery tube may be fluidly coupled to the tool, wherein the delivery tube may be configured to deliver fluid to the tool; the flexible delivery tube may at least partially extend through the lumen; the flexible delivery tube may include a flexible distal portion formed of an inner coil covered by an outer polymeric sheath; the pivoting member may be held by the clevis and rotatable relative to the clevis; the pivoting member may include at least one proximally directed tang, and at least one control member may be connected to the at least one proximally directed tang; and the tool may be deflected in a first direction when the control member is distally advanced, and the tool may be deflected in a second direction opposite the first direction when the control member is proximally retracted.

In accordance with yet another embodiment, a medical device may include a flexible elongate member; a tool configured to conduct electricity and deliver a fluid; a pivoting member, wherein the tool is operably coupled to the pivoting member; a first control member operably coupled to the pivoting member at a first side of the pivoting member; and a second control member operably coupled to the pivoting member at a second side of the pivoting member opposite the first side, wherein the tool may be configured to pivot towards either side of the elongate member by actuation of the first and second control members.

Various embodiments of the disclosure may include one or more of the following aspects: a flexible delivery tube fluidly coupled to the tool between the first and second sides of the pivoting member, wherein the delivery tube may be configured to deliver fluid to the tool; the tool may be deflected in a first direction when the first control member is proximally retracted, and the tool may be deflected in a second direction opposite the first direction when the second control member is proximally retracted; and the flexible delivery tube may include a flexible distal portion formed of an inner coil covered by an outer polymeric sheath.

In this respect, before explaining multiple embodiments of the present disclosure in detail, it is to be understood that the present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as the abstract, are for the purpose of description and should not be regarded as limiting.

The accompanying drawings illustrate certain exemplary embodiments of the present disclosure, and together with the description, serve to explain the principles of the present disclosure. As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

DETAILED DESCRIPTION

Reference will now be made in detail to the exemplary embodiments of the present disclosure described above and illustrated in the accompanying drawings.

The terms "proximal" and "distal" are used herein to refer to the relative positions of the components of an exemplary endoscopic instrument. When used herein, "proximal" refers to a position relatively closer to the exterior of the body or closer to the physician, or other user, using the endoscopic instrument. In contrast, "distal" refers to a position relatively further away from the surgeon, or other user, using the endoscopic instrument or closer to the interior of the body.

Figure 1:
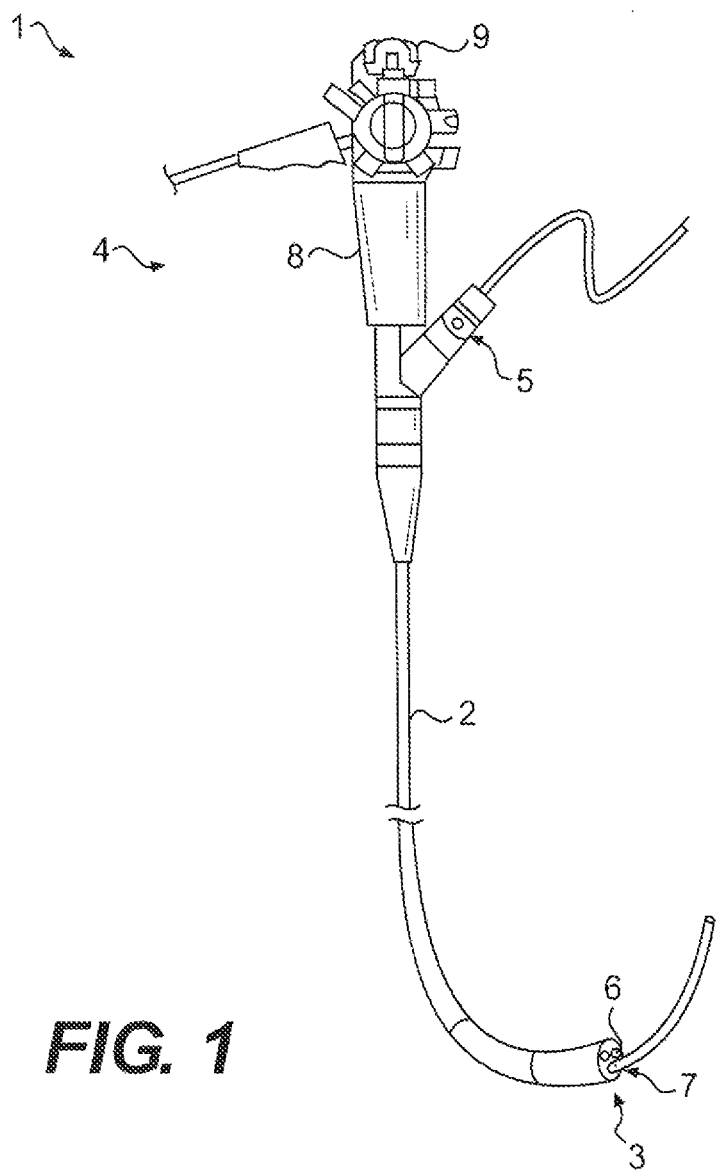
FIG. 1 illustrates an endoscope for use with an injection needle, according to an exemplary disclosed embodiment.

FIG. 1 illustrates an endoscope 1 according to an exemplary embodiment. Endoscope 1 may include a flexible outer tube 2 extending between a distal end 3 and a proximal end 4 of endoscope 1. Endoscope 1 may further include at least one treatment instrument port 5 for receiving a treatment device, such as a suction device, an injection needle, electrocautery needle, forceps, and any other suitable device known in the art, into at least one working channel 6 of endoscope 1. The at least one working channel 6 may extend within endoscope 1 and terminate at distal end 3 at an opening 7. Although opening 7 is illustrated as being defined on a distal face of outer tube 2, it should also be appreciated that one or more openings 7 may be defined on a side surface of outer tube 2.

Endoscope 1 may also include a handle 8 at proximal end 4. Handle 8 may include various positioning controls 9 to effectuate bending and rotation of flexible outer tube 2 for positioning endoscope 1 and any treatment instruments during a medical procedure.

The present disclosure may relate to endoscopic instruments that may include various types of end effectors, or tools, at the distal end of the endoscopic instrument that may require precise positioning within an anatomical lumen. The present disclosure describes embodiments of injection needles. Other types of tools, however, may be substituted for the injection needle, including, as examples, biopsy forceps, graspers, scissors, knives, probes, dissectors, scrapers, cautery electrodes, and suction probes.

Figure 2A:
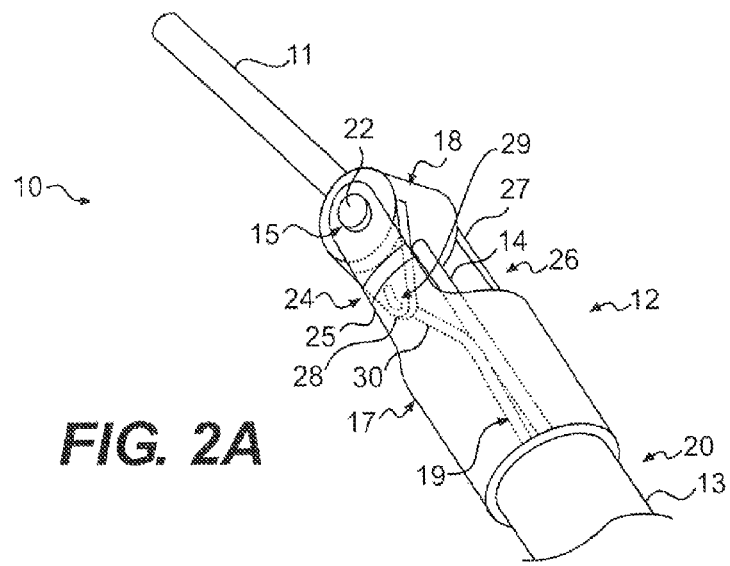
FIG. 2A illustrates a schematic view of an injection needle, according to an exemplary disclosed embodiment.
Figure 2B:
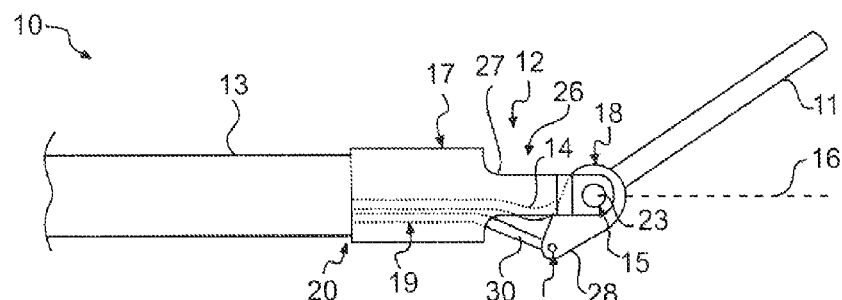
FIG. 2B illustrates another schematic view of the injection needle of FIG. 2A, according to an exemplary disclosed embodiment.
Figure 2C:
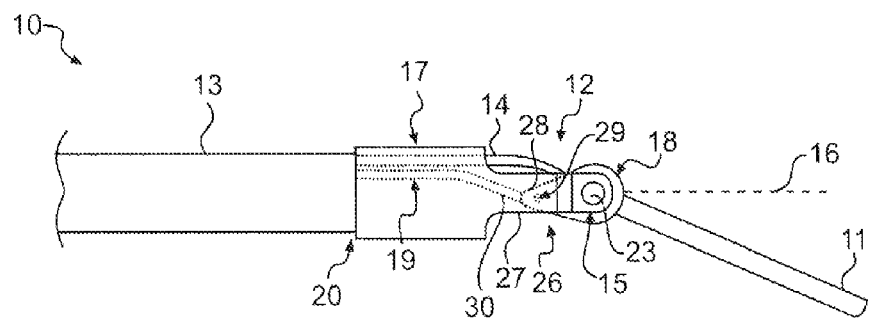
FIG. 2C illustrates another schematic view of the injection needle of FIG. 2A, according to an exemplary disclosed embodiment.

FIGS. 2A-2C illustrate an injection needle 10 according to an exemplary disclosed embodiment. Injection needle 10 may extend through the at least one working channel 6 of endoscope 1 and exit opening 7 to reach a desired treatment location. Injection needle 10 may be configured to, for example, irrigate fluids at a treatment site, inject vasoconstrictor fluid into a vessel to slow hemorrhaging, inject a sclerosing agent to control bleeding varices by hardening targeted tissues, inject suitable fluids for creating a bleb at the treatment location, inject fluids into tissue at the treatment location to separate tissue planes, inject fluidic dyes, such as Indigo Carmine, for visualization purposes, inject drugs, and inject bulking agents. In certain other embodiments, injection needle 200 may be configured to aspirate fluids and/or tissue.

As illustrated in FIG. 2A, injection needle 10 may include a distal tool 11, a positioning mechanism 12, and a flexible tube 13. Distal tool 11 may be hollow and include a lumen fluidly coupled to a delivery tube 14 extending through flexible tube 13. In some embodiments, distal tool 11 may be a hypotube. A flexible stylet may be positioned in the lumen of distal tool 11 to provide structural strength for distal tool 11 and block the entry of tissue. A suitable fluid may be delivered from a fluid source (not shown), through delivery tube 14, and out of a distal opening of distal tool 11. Distal tool 11 may be formed of any material capable of conducting electricity, such as, for example, stainless steel, nickel titanium alloys, and the like. A distal end of distal tool 11 may be relatively sharp for piercing tissue. Alternatively, the distal end of distal tool 11 may be relatively blunt and may penetrate tissue via an electrical current running through distal tool 11, as will be described in more detail below. By being relatively blunt, injection needle 10 may be advanced through the at least one working channel 6 of endoscope 1 without skiving the walls of channel 6. A proximal end of distal tool 11 may be operably coupled to positioning mechanism 12.

Positioning mechanism 12 may be configured to rotate, or deflect, distal tool 11 of injection needle 10 around a pivot axis 15. In other words, and as shown in FIGS. 2B-2C, distal tool 11 may pivot in a lateral direction relative to a longitudinal axis 16 of flexible tube 13 by actuation of positioning mechanism 12. Positioning mechanism 12 may include a clevis member 17, a pivoting member 18, and a control member 19. Control member 19 may include any suitable coupling device, such as, for example, a wire, a rod, or a hollow tube.

Clevis member 17 may be disposed on a distal end 20 of flexible tube 13. A proximal portion of clevis member 17 may be positioned over flexible tube 13 and may be hollow to provide communication between flexible tube 13 and tang portion 18. Alternatively, the proximal portion of clevis member 17 may be under (or within) flexible tube 13, or abut against flexible tube 13.

Pivoting member 18 may be positioned within clevis member 17 and may be coupled to clevis member 17 via a first pin (or boss) 22 and a second pin (or boss) 23. First pin 22 may extend from a first side 24 of pivoting member 18 and may rotatably connect pivoting member 18 to a first arm 25 of clevis member 17. Second pin 23 may extend from a second side 26 of pivoting member 18 and may rotatably connect pivoting member 18 to a second arm 27 of clevis member 17. Accordingly, pivoting member 18 may be configured to rotate about first pin 22 and second pin 23. Pivoting member 18 may include a lumen extending to distal tool 11. The lumen may be fluidly coupled to distal tool 11 such that fluid may be delivered through distal tool 11. In one example, delivery tube 14 may partially extend through the lumen of pivoting member 18 and may be fluidly coupled to distal tool 11. In certain other embodiments, delivery tube 14 may extend through the lumen and may be directly connected to distal tool 11 by any suitable means, such as, for example, adhesives, welding, friction fit, crimping, and the like. Alternatively, delivery tube 14 and distal tool 11 may be integrally formed, in which distal tool 11 may be a rigid extension of delivery tube 14. In another example, delivery tube 14 may terminate on an exterior surface of pivoting member 18 and may be fluidly coupled to a proximal opening of the lumen. Accordingly, fluid may travel from delivery tube 14, into the first lumen, and out of distal tool 11. Delivery tube 14 may be composed of one or more of metals, plastics, polymers, and elastomers, and may be formed of multiple materials to vary the flexibility and the stiffness along delivery tube 14. In certain embodiments, a distal portion of delivery tube 14 may be more flexible then a proximal portion of delivery tube 14 to accommodate bending. For example, the distal portion of delivery tube 14 may be formed of a metallic spring or coil covered by a flexible material, such as a polymeric sheath, and the proximal portion of delivery tube 14 may be formed of a stiff, polymeric tube.

Pivoting member 18 may also include a proximally extending coupling element in the form of a tang 28. Tang 28 and control member 19 may be positioned proximate first side 24, or alternatively second side 26, of pivoting member 18 to provide a substantially central access for delivery tube 14 to distal tool 11. Tang 28 may be, for example, a fin-shaped protrusion coupled to control member 19 at a coupling point 29. Coupling point 29 between control member 19 and tang 28 may be any suitable pivoting arrangement. For example, control member 19 may extend through a hole on a side surface of tang 28 and may be crimped to secure member 19 to tang 28. The hole may have a diameter larger than the diameter of member 19 to allow suitable rotation of member 19 within the hole. Accordingly, as control member 19 is pushed forward (FIG. 2B) or pulled back (FIG. 2C), control member 19 and coupling member 28 may pivot relative to one another at coupling point 29.

An appropriate handle assembly (not shown) may be operably coupled to control member 19 external endoscope 1 and may manipulate control member 19. Any suitable, known handle may be used, including spool-type handles or scissor-like handles. Control member 19 may be actuated to advance in a distal direction, as shown in FIG. 2B. In other words, control member 19 may be pushed forward, causing control member 19 to pivot relative to tang 28 and rotate pivoting member 18, resulting in the deflection of distal tool 11 in a first direction. As shown in FIG. 2C, control member 19 may be retracted in a proximal direction (i.e., pulled backward), causing control member 19 to pivot relative to tang 28 and rotate pivoting member 18 in the opposite direction, resulting in the deflection of distal tool 11 in a second direction opposite the first direction. Therefore, an angle between distal tool 11 and longitudinal axis 16 may be altered upon actuation of control member 19. Deflection of distal tool 11, if desired, may be restricted through any number of suitable stop structures. For example, one or more of flexible tube 13, clevis member 17, control member 19, tang 28, and coupling point 29 may be dimensioned such that control member 19 abuts against either clevis member 17 or the internal wall of flexible tube 13 when distal tool 11 reaches predetermined angles relative to longitudinal axis 16.

Control member 19 may also include a bent portion 30. FIG. 2B illustrates that as control member 19 is distally advanced, bent portion 30 may extend external clevis member 17 at an angle offset from longitudinal axis 16, while the portion of control member 19 proximal bent portion 30 moves towards the internal wall of flexible tube 13. Because control member 19 may pivot relative to tang 28, and bent portion 30 may extend from clevis member 17 at an angle, tang 28 may in turn significantly deflect out of the slot defined between first and second arms 25, 27 of clevis member 17. Therefore, pivoting member 18 may have an increased angular rotation, allowing distal tool 11 to have a greater range of motion when control member 19 is distally advanced.

The bent portion 30 may also restrict the range of motion of distal tool 11 when control member 19 is proximally retracted. As shown in FIG. 2C, when control member 19 is proximally retracted, control member 19 may pivot relative to tang 28, and bent portion 30 may be retracted into clevis member 17. Bent portion 30, however, may restrict tang 28 from movement outside of the slot defined between first and second arms 25, 27. Pivoting member 18 may therefore have a decreased angular rotation, and thus distal tool 11 may have a smaller range of motion when control member 19 is proximally retracted relative to when control member 19 is distally advanced.

Accordingly, as the bend of control member 19 becomes larger (i.e., the bend angle between bent portion 30 and the rest of control member 19 becomes smaller), the range of motion of distal tool 11 when control member 19 is distally advanced may become greater, but the range of motion of distal tool 11 when control member 19 is proximally retracted may become smaller. Such a configuration may have certain advantages. For example, it may be beneficial for distal tool 11 to have an increased range of motion in one direction to reach and treat targeted tissue, while limiting the range of motion in the opposite direction to prevent distal tool 11 from contacting and damaging healthy tissue. Furthermore, the arrangement of tang 28 with bent portion 30 provides a collapsed and compact configuration for positioning mechanism 12. That is, substantial portions of control member 19 and tang 28 may be housed within clevis member 17, thereby preventing, for example, undesired snagging of tissue. It should also be appreciated that by increasing the length of bent portion 30, the range of motion when control member 19 is distally advanced may become greater, and the range of motion of distal tool 11 when control member 19 is proximally retracted may become smaller. In addition, varying the flexibility of bent portion 30 may affect the range of motion of distal tool 11. For example, forming bent portion 30 of a more flexible material relative to the rest of control member 19 may allow bent portion 30 to bend or deflect as control member 19 is proximally retracted and distally advanced. Therefore, increasing the flexibility of bent portion 30 may increase the range of motion of distal tool 11 when control member 19 is both proximally retracted and distally advanced.

As discussed above, distal tool 11 may be electrically conductive to act as a electrosurgical treatment instrument. For example, distal tool 11 may coagulate, cauterize, dissect, burn, and/or cut target tissue upon being energized by an electrical current. Moreover, distal tool 11 may be configured to perform monopolar or bipolar cauterization. Such electrosurgical treatment by distal tool 11 may be performed as distal tool 11 is deflected about pivot axis 15. In addition, the electrosurgical treatment by distal tool 11 may be performed in conjunction with the fluid delivery feature of injection needle 10. For example, fluid may be injected though distal tool 11 at a tissue treatment site to separate certain tissue layers, such as an adenoma from its underlying tissue. Distal tool 11 may then become electrically activated and cauterize and resect the adenoma.

In one exemplary embodiment, control member 19 may provide an electrical pathway from a source of electrical current (not shown) to distal tool 11. The handle assembly may include an appropriate connector for connection to, for example, a source of radio frequency (RF) energy. The energy may be conducted through the handle assembly to control member 19. Control member 19 and pivoting member 18, including tang 28, may be formed of any material capable of conducting electricity, such as, for example, stainless steel, nickel titanium alloys, and the like. Contact between distal tool 11 and pivoting member 18 may provide an electrical connection for electricity delivered through control member 19. Additionally, or alternatively, a separate conductive wire, cable, or the like may be twisted along, adjacent to, or formed within control member 19 and may provide the electrical pathway to distal tool 11. Clevis member 17 may also be formed of any material capable of conducting electricity; however, the surface of clevis member 17 may be covered with a suitable insulating material, such as, for example a powder coat or non-conducting polymeric sheath, to minimize the discharge and effects of any stray electrical energy from clevis member 17. Insulation of clevis member 17 may also prevent electrical energy from causing tissue damage due to incidental contact with clevis member 17. Similarly, flexible tube 13 may be formed of any non-conducting polymer material, or may be coated with an insulating polymer material incapable of conducting electricity.

It should also be appreciated that control member 19 and pivoting member 18 may be covered with a suitable insulating material. For example, an insulating sheath may cover control member 19, and the surface of pivoting member 18 may be powder coated with an insulating material.

Additionally, or alternatively, delivery tube 14 may provide an electrical pathway from the source of electrical current to distal tool 11. In such an arrangement, delivery tube 14 may include a coil or a wire formed of any suitable material capable of conducting electricity in direct contact with distal tool 11. A sheath formed of an insulating polymer material may cover the coil to prevent the discharge and effects of stray electrical energy from delivery tube 14. In another embodiment, delivery tube 14 may be a sheath formed of an insulating polymer material. A conductive wire may be attached to an interior wall of the sheath and may be directly connected to distal tool 11, thereby providing an electrical path from the source of electrical current to distal tool 11. Alternatively, the conductive wire may be attached to an outside surface of the sheath and may be electrically connected to pivoting member 18. Electrical energy may therefore travel from pivoting member 18 to distal tool 11. It should be appreciated that the conductive wire may also be covered with a suitable insulating material to prevent the discharge and effects of any stray electrical energy.

Figure 3A:
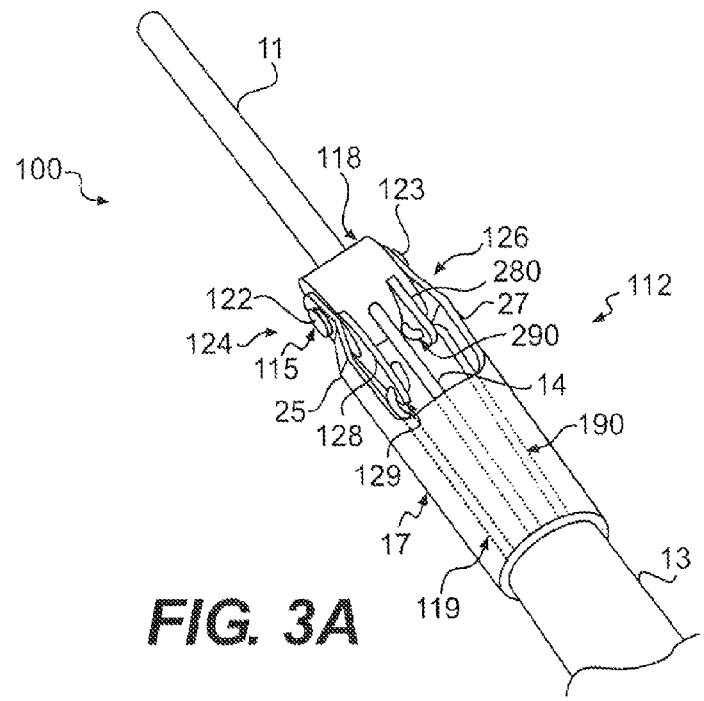
FIG. 3A illustrates a schematic view of another injection needle, according to an exemplary disclosed embodiment.
Figure 3B:
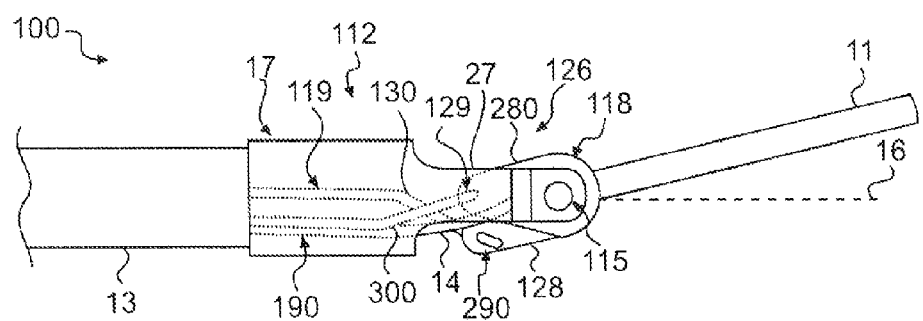
FIG. 3B illustrates another schematic view of the injection needle of FIG. 3A, according to an exemplary disclosed embodiment.
Figure 3C:
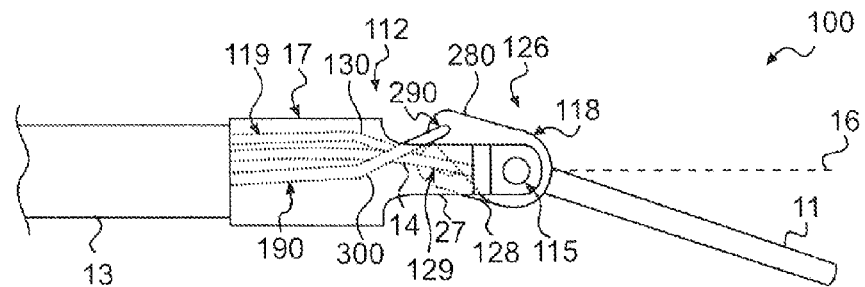
FIG. 3C illustrates another schematic view of the injection needle of FIG. 3A, according to an exemplary disclosed embodiment.

FIGS. 3A-3C illustrate another embodiment of an injection needle 100. Similar to the embodiments of FIGS. 2A-2C, injection needle 100 may include a flexible tube 13 and a distal tool 11 fluidly coupled to delivery tube 14. Injection needle 100 may also include a positioning mechanism 112 configured to deflect distal tool 11 around a pivot axis 115. Similar to the embodiments of FIGS. 2A-2C, positioning mechanism 112 may include clevis member 17. In addition, positioning mechanism 112 may include a pivoting member 118, a first control member 119, and a second control member 190. Like control member 19, first and second control members 119, 190 may include any suitable coupling device, such as, for example, a wire, a rod, or a hollow tube.

Pivoting member 118 may be positioned within clevis member 17 and coupled to clevis member 17 via a first pin (or boss) 122 and a second pin (or boss) 123. First pin 122 may extend from a first side 124 of pivoting member 118 and may rotatably connect pivoting member 118 to first arm 25 of clevis member 17. Second pin 123 may extend from a second side 126 of pivoting member 118 and may rotatably connect pivoting member 118 to second arm 27 of clevis member 17. Accordingly, pivoting member 118 may be configured to rotate about first pin 122 and second pin 123. Delivery tube 14 may be fluidly coupled to distal tool 11, similar to the embodiments of FIGS. 2A-2C.

Pivoting member 118 may also include a first coupling element in the form of a tang 128 proximate first pin 122 and a second coupling element in the form of a tang 280 proximate second pin 123. Delivery tube 14 may be fluidly coupled to distal tool 11 between tangs 128, 280. Tangs 128, 280 may be, for example, fin-shaped protrusions. Tang 128 may be coupled to first control member 119 at a first coupling point 129, and tang 280 may be coupled to second control member 190 at a second coupling point 290. First and second coupling points 129, 290 may be any suitable pivoting arrangement. Accordingly, as first control member 119 is pushed forward (FIG. 3B) or pulled back (FIG. 3C), first control member 119 and tang 128 may pivot relative to one another at first coupling point 129. Moreover, as second control member 190 is pushed forward (FIG. 3C) or pulled back (FIG. 3B), second control member 190 and second control element 280 may pivot relative to one another at second coupling point 290.

An appropriate handle assembly (not shown) may be operably coupled to first control member 119 and second control member 190 external endoscope 1 and may manipulate first and second control members 119, 190. For example, and as shown in FIG. 3B, the handle assembly may be actuated to advance first control member 119 in a distal direction, while simultaneously retracting second control member 190 in a proximal direction. That is, first control member 119 may be pushed forward, and second control member 190 may be pulled back, causing first and second control members 119, 190 to pivot relative to tangs 128, 280, respectively, and rotate pivoting member 118, resulting in the deflection of distal tool 11 in a first direction.

As shown in FIG. 3C, the handle assembly may be actuated to retract first control member 119 in a proximal direction, while simultaneously advancing second control member 290 in a distal direction. In other words, first control member 119 may be pulled back, and second control member 190 pushed forward, causing first and second control members 119, 190 to pivot relative to tangs 128, 280, respectively, and rotate pivoting member 118, resulting in the deflection of distal tool 11 in a second direction opposite the first direction. Thus, an angle between distal tool 11 and the longitudinal axis 16 of flexible tube 13 may be altered upon actuation of first and second control members 119, 190. Deflection of distal tool 11, however, may be restricted once either of first control member 119 or second control member 190 abuts against clevis member 17 or the internal wall of flexible tube 13. In certain embodiments, one or more of tang 128, tang 280, and clevis member 17 may include a protrusion or the like to limit rotational movement of pivoting member 118 by, for example, abutting against clevis member 17 or tangs 128, 280.

First control member 119 may include a bent portion 130, and second control member 190 may include a bent portion 300. As shown in FIGS. 3B and 3C, bent portion 130 and bent portion 300 may point in opposite directions. Moreover, the bend angle between bent portion 130 and the rest of first control member 119 may be substantially the same as the bend angle between bent portion 300 and the rest of second control member 190. In addition, tang 128 and tang 280 may have a staggered configuration, wherein, when distal tool 11 is substantially aligned with longitudinal axis 16, tang 128 (and particularly its coupling point 129) may be on one side of longitudinal axis 16 (e.g., above longitudinal axis 16), and tang 280 (and particularly its coupling point 290) may be on the other side of longitudinal axis 16 opposite tang 128 (e.g., below longitudinal axis 16). Such a staggered configuration may accommodate the opposite directions to which bent portion 130 and bent portion 300 extend. As such, the range of motion when distal tool 11 is deflected in the first direction is substantially the same as the range of motion when distal tool 11 is deflected in the second direction. Moreover, in certain embodiments, distal tool 11 may be deflected as much as 90 degrees relative to longitudinal axis 16 in either direction. It should also be appreciated that tangs 128, 280 may be any suitable shape to increase or decrease the leverage of first and second control members 119, 190 in rotating pivoting member 118. For example, a long and thin shape of tangs 128, 280 may increase the leverage of first and second control members 119, 190. In addition, the position and/or the strength of connection points 129, 290 may increase or decrease the leverage of first and second control members 119, 190 in rotating pivoting member 118.

Such a configuration may have certain advantages. For example, because the range of motion of distal tool 11 may be large and substantially the same in both directions of deflection, injection needle 11 may have increased maneuverability, which may be advantageous when manipulating injection needle 100 in tortuous anatomies of the body. In addition, the increased maneuverability of distal tool 11 allows a greater area of tissue on both sides of distal tool 11 to be treated. Furthermore, and similar to the embodiments of FIGS. 2A-2C, the arrangement of tangs 128, 280 with bent portions 130, 300 provides a collapsed and compact configuration for positioning mechanism 112.

As discussed, distal tool 11 may be electrically conductive to act as a electrosurgical treatment instrument. Similar to the embodiments of FIGS. 2A-2C, one or both of first control member 119 and second control member 190 may provide an electrical pathway from a source of electrical current (not shown) to distal tool 11. As such, first control member 119, second control member 190, and pivoting member 118, including tangs 128, 280, may be formed any material capable of conducting electricity, such as, for example, stainless steel, nickel titanium alloys, and the like. Additionally, or alternatively, a separate conductive wire, cable, or the like may be twisted along, adjacent to, or formed within one or both of first control member 119 and second control member 190 and may provide the electrical pathway to distal tool 11. Contact between distal tool 11 and pivoting member 118 may provide an electrical connection for electricity delivered through one or both of first control member 119 and second control member 190. It should also be appreciated that first and second control members 119, 190 and pivoting member 118 may be covered with a suitable insulating material.

Additionally, or alternatively, delivery tube 14 may provide an electrical pathway from the source of electrical current to distal tool 11, in a similar manner as the embodiments of FIGS. 2A-2C.

Figure 4A:
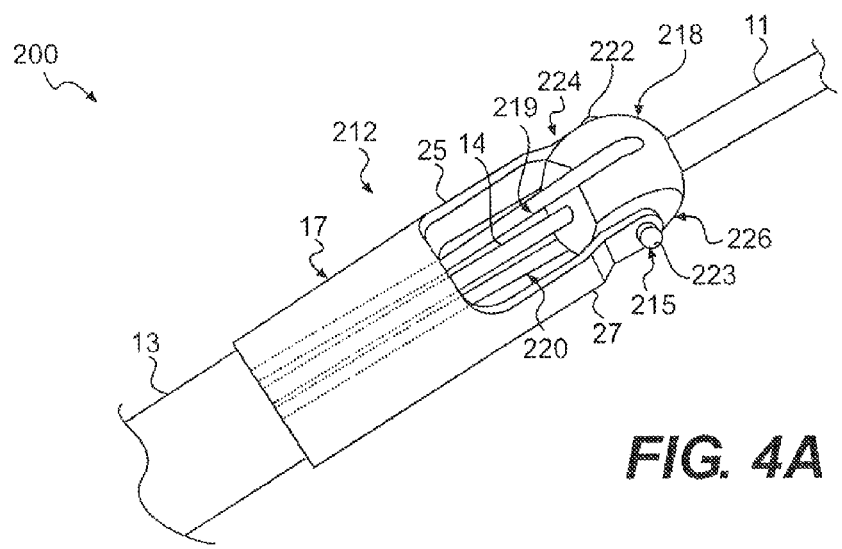
FIG. 4A illustrates a schematic view of another injection needle, according to an exemplary disclosed embodiment.
Figure 4B:
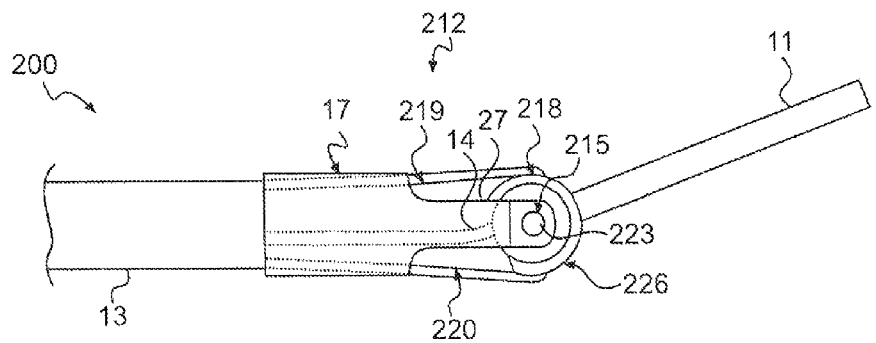
FIG. 4B illustrates another schematic view of the injection needle of FIG. 4A, according to an exemplary disclosed embodiment.
Figure 4C:
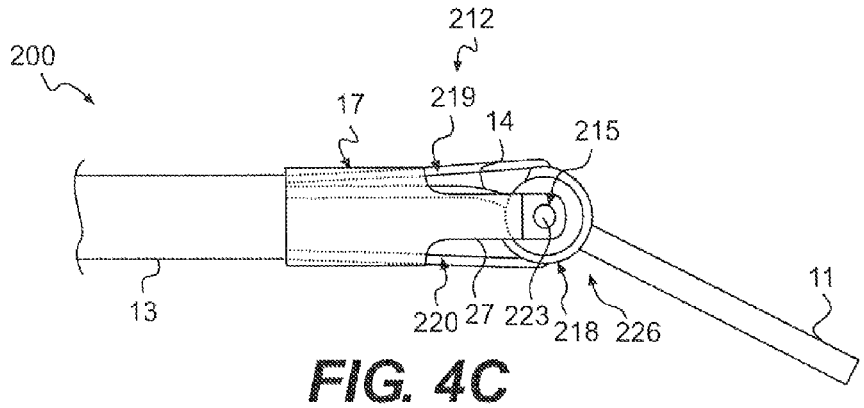
FIG. 4C illustrates another schematic view of the injection needle of FIG. 4A, according to an exemplary disclosed embodiment.

FIGS. 4A-4C illustrate another embodiment of an injection needle 200. Similar to the embodiments of FIGS. 2A-3C, injection needle 200 may include flexible tube 13 and distal tool 11 fluidly coupled to delivery tube 14. Injection needle 200 may also include a positioning mechanism 212 configured to deflect distal tool 11 around a pivot axis 215. Similar to the embodiments of FIGS. 2A-3C, positioning mechanism 212 may include clevis member 17. In addition, positioning mechanism 212 may include a pivoting member 218, a first control member 219, and a second control member 220. Like control member 19 and first and second control members 119, 190, first and second control members 219, 220 may include any suitable coupling device, such as, for example, a wire, a rod, or a hollow tube.

Pivoting member 218 may be positioned within clevis member 17 and coupled to clevis member 17 via a first pin (or boss) 222 and a second pin (or boss) 223. First pin 222 may extend from a first side 224 of pivoting member 218 and may rotatably connect pivoting member 218 to first arm 25 of clevis member 17. Second pin 223 may extend from a second side 226 of pivoting member 218 and may rotatably connect pivoting member 218 to second arm 27 of clevis member 17. Accordingly, pivoting member 218 may be configured to rotate about first pin 222 and second pin 223. Delivery tube 14 may be fluidly coupled to distal tool 11, similar to the embodiments of FIGS. 2A-2C.

A distal portion of first control member 219 may be anchored to pivoting member 218 on a first surface of pivoting member 218, and a distal portion of second control member 220 may be anchored to pivoting member 218 on a second surface opposite the first surface of pivoting member 218. First and second control members 219, 220 may be anchored to pivoting member 218 by any suitable means such as, for example, adhesives, welding, crimping, and the like. Moreover, first and second control members 219, 220 may be substantially aligned with each other and may be defined on opposite sides of distal tool 11. In addition, delivery tube 14 may be fluidly coupled to distal tool 11 between first and second control members 219, 220.

An appropriate handle assembly (not shown) may be operably coupled to first control member 219 and second control member 220 external endoscope 1 and may manipulate first and second control members 219, 220. For example, and as shown in FIG. 4B, the handle assembly may be actuated to retract first control member 219 in a proximal direction. That is, first control member 219 may be pulled back, causing pivoting member 218 to rotate, and thus the deflection of distal tool 11 in a first direction. As shown in FIG. 4C, the handle assembly may be actuated to retract second control member 220 in a proximal direction (i.e., pulled back), causing pivoting member 218 to rotate, and thus the deflection of distal tool 11 in a second direction opposite the first direction.

Positioning mechanism 212 may provide an increased range of motion for distal tool 11. That is, distal tool 11 may be deflected in the first and second directions without being bound by first control member 219 or second control member 220 abutting against clevis member 17 or the internal wall of flexible tube 13. In addition, no component of pivot 218 will extend radially outwards, like tangs 28, 128, and 280 of the prior embodiments. Accordingly, such increased maneuverability of distal tool 11 allows a greater area of tissue on both sides of distal tool 11 to be treated. Moreover, the increased range of motion may allow distal tool 11 to be proximally deflected and collapsed in a "switch blade" type configuration. Such a collapsed configuration may avoid skiving of the at least one working channel 6 as injection needle 200 is delivered therethrough. It should be appreciated, however, that injection needle 200 may include any suitable restriction means to regulate the range of motion of distal tool 11. For example, the handle assembly may include appropriate stops configured to limit the length of first control member 219 and/or second control member 220 that may be retracted.

Similar to the embodiments of FIGS. 2A-3C, one or both of first control member 219 and second control member 220 may provide an electrical pathway from a source of electrical current (not shown) to distal tool 11. As such, first control member 219, second control member 220, and pivoting member 218 may be formed any material capable of conducting electricity, such as, for example, stainless steel, nickel titanium alloys, and the like. Additionally, or alternatively, a separate conductive wire, cable, or the like may be twisted along, adjacent to, or formed within one or both of first control member 219 and second control member 220 and may provide the electrical pathway to distal tool 11. Contact between distal tool 11 and pivoting member 218 may provide an electrical connection for electricity delivered through one or both of first control member 219 and second control member 220. It should also be appreciated that first and second control members 219, 220 and pivoting member 219 may be covered with a suitable insulating material.

Additionally, or alternatively, delivery tube 14 may provide an electrical pathway from the source of electrical current to distal tool 11, in a similar manner as the embodiments of FIGS. 2A-3C.

It should also be appreciated that the handle assembly for any of injection needles 10, 100, and 200 may include an appropriate locking mechanism to lock distal tool 11 in any suitable position. For example, the locking mechanism may secure distal tool 11 in a deflected position, and may release the distal tool 11 from the deflected position when desired.

As will be appreciated by one of ordinary skill in the art, the presently disclosed injection needles 10, 100, and 200 may enjoy numerous advantages. First, for example, distal tool 11 may be adjusted independently of endoscope 1, that is, the position of distal tool 11 may be altered by manipulating positioning mechanism 12, 112, or 212, without the need to articulate, steer, shift, pull, and/or push endoscope 1. Therefore, finer control of the position of distal tool 11 may be provided to a physician. In addition, the physician may be able to maneuver and control injection needle 10, 100, and 200, without assistance from a second operator, such as another physician or a physician's assistant. The physician may directly and simultaneously control the position and activation (i.e., fluid delivery and electrocauterization) of injection needle 10, 100, and 200. Moreover, when using injection needle 10, 100, or 200 with an endoscope housing multiple tools, the position of injection needle 10, 100, or 200 may be independently controlled without moving the other tools, since the entire endoscope need not be manipulated to position injection needle 10, 100, or 200.

In certain other embodiments, the distal tool may serve as a guide for other endoscopic tools inserted into body anatomies. For example, an electrocautery loop may be fed through an insertion tube coupled to the distal tool. The electrocautery loop may then exit the distal tool to reach target tissue. By actuating the positioning mechanism, the distal tool, and thus the electrocautery loop, may be deflected to a desired position.

Moreover, it should be appreciated that any of devices 10, 100, and 200 may include an imaging system for visualizing the body anatomies. The imaging system may include any suitable system for capturing images within body anatomies, such as, for example, an optical fiber and/or an electronic camera including illumination units. Accordingly, devices 10, 100, and 200 may then be used without endoscope 1 for visualization purposes. Nevertheless, employing devices 10, 100, and 200 having an imaging system with endoscope 1 may provide multiple areas of visualization, including one area from endoscope 1 and another area from devices 10, 100, and 200.

Any aspect set forth in any embodiment may be used with any other embodiment set forth herein. Every device and apparatus set forth herein may be used in any suitable medical procedure, may be advanced through any suitable body lumen and body cavity, and may be used for treatment of any suitable body portion. For example, the apparatuses and methods described herein may be used in any natural body lumen or tract, including those accessed orally, vaginally, or rectally.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. A medical device, comprising:
    a shaft having a central longitudinal axis, wherein the shaft includes a lumen;
    a tool assembly pivotably coupled to the shaft to pivot about a pivot axis to opposite sides of the central longitudinal axis, wherein the tool assembly includes a proximal end portion proximal to the pivot axis, and a distal end portion distal to the pivot axis, wherein the pivot axis provides a fulcrum between the proximal end portion and the distal end portion; and
    a control member extending through the lumen, wherein the control member is pivotably coupled to the proximal end portion, and movement of the control member in a distal direction pivots the distal end portion in a first direction from a first side of the central longitudinal axis to a second side of the central longitudinal axis, the first side and the second side being opposite sides of the central longitudinal axis.

2. The medical device of claim 1, wherein the control member is laterally offset from the central longitudinal axis.

3. The medical device of claim 1, wherein the control member includes a proximal portion, a distal portion, and a bent portion between the proximal portion and the distal portion, such that proximal portion extends at an angle relative to distal portion.

4. The medical device of claim 1, wherein the control member is a first control member, and the medical device further includes a second control member extending through the lumen, and wherein the second control member is pivotably coupled to the proximal end portion, and movement of the second control member in a proximal direction pivots the distal end portion in a second direction, the second direction being opposite the first direction.

5. The medical device of claim 1, wherein the pivot axis is perpendicular to the central longitudinal axis.

6. The medical device of claim 1, wherein the tool assembly includes one of a cylindrical body and a spherical body surrounding the pivot axis.

7. The medical device of claim 1, wherein the distal end portion includes an injection tube, and the proximal end portion includes a delivery tube extending through the lumen, and wherein the delivery tube is in fluid communication with the injection tube.

8. The medical device of claim 1, wherein the proximal end portion is fixed relative to the distal end portion.

9. A medical device, comprising:
    a shaft having a central longitudinal axis, wherein the shaft includes a lumen;
    a tool assembly pivotably coupled to the shaft to pivot about a pivot axis to opposite sides of the central longitudinal axis, wherein the tool assembly includes a proximal end portion extending proximal to the pivot axis and a distal end portion extending distal to the pivot axis, and the pivot axis provides a fulcrum between the proximal end portion and the distal end portion; and
    a control member extending through the lumen, wherein the control member is movably coupled to the proximal end portion such that movement of the control member in a distal direction pivots the distal end portion in a first direction from a first side of the central longitudinal axis to a second side of the central longitudinal axis, the first side and the second side being opposite sides of the central longitudinal axis, and wherein movement of the control member in a proximal direction pivots the distal end portion in a second direction, the second direction being opposite the first direction.

10. The medical device of claim 9, wherein the pivot axis is perpendicular to the central longitudinal axis.

11. The medical device of claim 9, wherein movement of the control member in the distal direction pushes the proximal end portion to pivot the distal end portion in the first direction, and movement of the control member in the proximal direction pulls the proximal end portion to pivot the distal end portion in the second direction.

12. The medical device of claim 9, wherein the control member includes a proximal portion, a distal portion, and a bent portion between the proximal portion and the distal portion, such that the proximal portion extends at an angle relative to the distal portion.

13. The medical device of claim 9, wherein the control member moves laterally across the lumen as the control member moves in at least one of the proximal direction and the distal direction.

14. The medical device of claim 9, wherein the control member is a first control member, and the medical device further includes a second control member movably coupled to the proximal end portion such that movement of the second control member selectively pivots the distal end portion in the first direction and the second direction.

15. The medical device of claim 9, wherein the proximal end portion is fixed relative to the distal end portion.

16. A medical device, comprising:
    a shaft having a central longitudinal axis, wherein the shaft includes a lumen;
    a tool assembly pivotably coupled to the shaft to pivot about a pivot axis to opposite sides of the central longitudinal axis, wherein the tool assembly includes a proximal end portion and a distal end portion, and the pivot axis provides a fulcrum between the proximal end portion and the distal end portion;
    a first control member extending through the lumen, wherein the first control member is movably coupled to the proximal end portion, and movement of the first control member in a distal direction drives pivoting of the distal end portion in a first direction from a first side of the central longitudinal axis to a second side of the central longitudinal axis, the first side and the second side being opposite sides of the central longitudinal axis; and
    a second control member extending through the lumen, wherein the second control member is movably coupled to the proximal end portion, and movement of the second control member in the distal direction drives pivoting of the distal end portion in a second direction, the second direction being opposite the first direction.

17. The medical device of claim 16, wherein the first control member and the second control member are each laterally offset from the central longitudinal axis.

18. The medical device of claim 16, wherein the first control member and the second control member are pivotably coupled to the proximal end portion.

19. The medical device of claim 16, wherein movement of the first control member in the proximal direction drives pivoting of the distal end portion in the second direction.

20. The medical device of claim 16, wherein the proximal end portion is fixed relative to the distal end portion.

* * * * *